US005374559A

United States Patent [19]

Devienne

[11] Patent Number: 5,374,559

[45] Date of Patent: Dec. 20, 1994

[54] PROCESS FOR THE SEQUENTIAL OBSERVATION OF THE SUCCESSIVE STATES OF A CHEMICAL REACTION

[76] Inventor: F. Marcel Devienne, 117, la Croisette, 06400 Cannes, France

[21] Appl. No.: 94,148

[22] PCT Filed: Dec. 16, 1992

[86] PCT No.: PCT/FR92/01190

§ 371 Date: Aug. 3, 1993

§ 102(e) Date: Aug. 3, 1993

[87] PCT Pub. No.: WO93/12535

PCT Pub. Date: Jun. 24, 1993

[30] Foreign Application Priority Data

Dec. 17, 1991 [FR] France .............................. 91 15648

[51] Int. Cl.[5] .............................................. G01N 33/00

[52] U.S. Cl. ...................................... 436/34; 436/173; 250/286

[58] Field of Search .................. 436/34, 173; 250/286; 315/111.8; 313/564

[56] References Cited

U.S. PATENT DOCUMENTS 4,608,344 8/1986 Carter et al. .......................... 436/34

FOREIGN PATENT DOCUMENTS 0430774 6/1991 European Pat. Off. .

2195349 3/1974 France .

2143673 2/1985 United Kingdom .

*Primary Examiner*—Nina Bhat

*Attorney, Agent, or Firm*—Oblon, Spivak, McClelland, Maier & Neustadt

[57] ABSTRACT

Process for the sequential observation of the successive states of a chemical reaction taking place in a high vacuum or under a low pressure or the determination of the nature of a substance or the composition of a mixture which can be liquid, solid or gaseous, or alternatively aerosols contained in air, by dissociation in a dissociation box or case (20) filled with a neutral gas from the molecules of the compounds formed, followed by energy filtration of the dissociation fragments in an electrostatic analyzer (22) and detector (24), characterized in that the molecules of the compounds to be analyzed are formed on a target (4), whose conductive walls are raised to a high d.c. voltage, the target (4) being bombarded by two molecular guns supplying high energy, neutral molecular jets (or mixtures of ions and neutral jets or only ions), namely a first continuous jet (16) supplying atoms and molecules for reacting together and/or with the target, and a second intermediate jet (18) of neutral gas molecules for ionizing, by impact, the molecules formed. The apparatus is such that in most cases the beams of neutral gases and secondary ions are in the same vertical plane.

4 Claims, 3 Drawing Sheets

PROCESS FOR THE SEQUENTIAL OBSERVATION OF THE SUCCESSIVE STATES OF A CHEMICAL REACTION

The main object of the invention is a process for the sequential observation of the successive states of a chemical reaction taking place in a vacuum or at low pressure, as well as the analysis of solids, liquids and gases (under certain conditions) and aerosols.

The study of the chemical reactions occurring between various compounds in a relatively high vacuum is useful e.g. for reconstituting the formation stages as from simple elements of organic or biological compounds. These reactions generally take place relatively rapidly and it is necessary, in order to be able to follow these syntheses, to have an apparatus making it possible to study in real time the formation phenomena of the organic compounds and in particular those used as a basis for living matter.

The present invention specifically relates to a process for the observation of the successive stages of a chemical reaction taking place in vacuum meeting the above requirements.

The process according to the invention makes use of known molecular ion dissociation methods by impact or shock on neutral gas molecules and the identification of the secondary dissociation atoms formed during the reaction. It is largely based on the processes described in FR-A-2 622 699 and FR-A-2 655 149, at least with respect to the analytical phase of the process using a dissociation box filled with a neutral gas and from which pass energy-filtered secondary ions into an electrostatic analyzer, whose filtration level is regulatable.

The sequential observation process for the successive states of a chemical reaction taking place in vacuum by dissociation in a dissociation box filled with a neutral gas of the molecules of the compounds formed, followed by energy filtration of the dissociation fragments in an electrostatic analyzer and detector is characterized in that the molecules of the compounds to be analyzed are formed on a target located in an enclosure, whose conductive walls are raised to a high d.c. voltage, the target being bombarded by two sources of high energy neutral molecular jets, namely a first continuous jet supplying the atoms and molecules for reacting together and/or with the target, and a second intermediate jet of neutral gas molecules for ionizing, by impact, the molecules formed; a system of extraction lenses being provided for extracting the ions formed and for passing them to the intake of the dissociation box, each intervention of the second jet thus making it possible to form on each occasion an image of the state of the reaction.

The originality of the process according to the invention is constituted by the simultaneous use of two high energy, neutral molecular jets and in that the axes of said jets are located in the same vertical plane during the performance of the process. The latter arrangement, which is preferred but not obligatory, more particularly makes it possible to work on liquids or powders contained in a small horizontal tank. The first supplies in continuous manner to the vacuum enclosure in which is located the target provided for this purpose the atoms and molecules, whose chemical reaction in the vacuum is to be studied. The second intermittent molecular jet is a jet of neutral gas molecules, e.g. argon, krypton or xenon, whose energy is such that it brings about the in situ, immediate ionization of the molecules as soon as they form and which by sputtering makes it possible to form a beam of secondary ions. Dissociation only subsequently occurs in the dissociation box provided for this purpose and on leaving which the secondary ion fragments formed are identified by their energy with the aid of the electrostatic analyzer.

Whereas the first jet, which can be referred to as a chemical jet, functions continuously supplying the atoms and molecules which it is wished to react together and/or with the target, the second jet is intermediate, so that to a certain extent it photographs the instantaneous evolution state of the chemical reaction taking place. Thus, for each intervention of the second intermittent jet, chemical molecules which have been formed are ionized and then immediately extracted from the reaction enclosure, dissociated in the dissociation chamber and analyzed by the analyzer-detector system. Precise estimates make it possible to affirm that between the ionization of a molecule and the detection and identification of the secondary ions formed, the time does not exceed a few microseconds, the ions being extracted at energy levels between 1000 and 15000 eV. As it is on the basis of the observation of the different secondary fragments detected that it is possible to identify the chemical molecule which has formed in the enclosure just prior to being ionized, it can be seen that the process, for each intervention of the second neutral gas molecular jet, provides a photograph of the state of the chemical reaction taking place and the appearance of the different compounds which it produces. This second molecular jet can also intervene on the basis of any desired, predetermined time programme, namely e.g. an intervention at a chosen time t or several successive interventions at chosen times, or even in pulsed form at a constant frequency. For example, the process can function with a second pulsed jet, whose period can evolve from $10^{-9}$ seconds to a few hundred seconds when this proves necessary. Obviously, the performance of the process requires a programming and a control by computer of a very precise nature of the intervention times of said second molecular jet.

According to a feature of the process according to the invention, the molecular jets have an energy of 0.5 to 15 keV and the vacuum enclosure is raised to potential of a few thousand volts, e.g. 1000 to 15000 V.

Moreover, the vacuum enclosure is placed at the pressure desired by the person carrying out the experiment for the precise study of a given reaction, but usually when it is wished to simulate the reactions liable to take place, e.g. in the intersideral space, said enclosure is raised to a very high vacuum, of approximately $10^{-6}$ to $10^{-9}$ Torr. It is also possible to have a higher limit vacuum by using two turbomolecular or drag pumps in series.

In order to simulate as faithfully as possible the conditions which can be those of reactions taking place in space, it can be of interest to reconstitute in the reaction enclosure parameters other than vacuum and subject same e.g. to a given temperature or to an ionizing radiation of a certain intensity. It is also possible to facilitate the ionization of heavy molecules (e.g. proteins) by bombarding with a nitrogen laser supplying a radius of wavelength 337 nm. The choice of the nature and the value of the different parameters is obviously left to the Expert and do not form part of the present invention.

BRIEF DESCRIPTION OF THE DRAWINGS

The invention will be better understood from the following description of non-limitative embodiments with reference to the attached FIGS. 1 to 3, wherein show:

FIG. 1 shows the vacuum enclosure 2 within which the process according to the invention is performed. It is merely a simple diagram, because the enclosure is much more complicated so that in particular the molecular guns can have the desired inclination with respect to the vertical axis of the body of the apparatus, so as to be able to bring about the same impact zone of both molecular jets on the target. In said vacuum enclosure, which can e.g. have a maximum volume of $30\times30$ liters, by means of a primary pump and a turbomolecular pump a high vacuum is maintained and possibly this can be up to $10^{-9}$ Torr (when the molecular guns are not operating) and in principle between $10^{-7}$ and $10^{-8}$ Torr when everything is operating.

Figure 1:
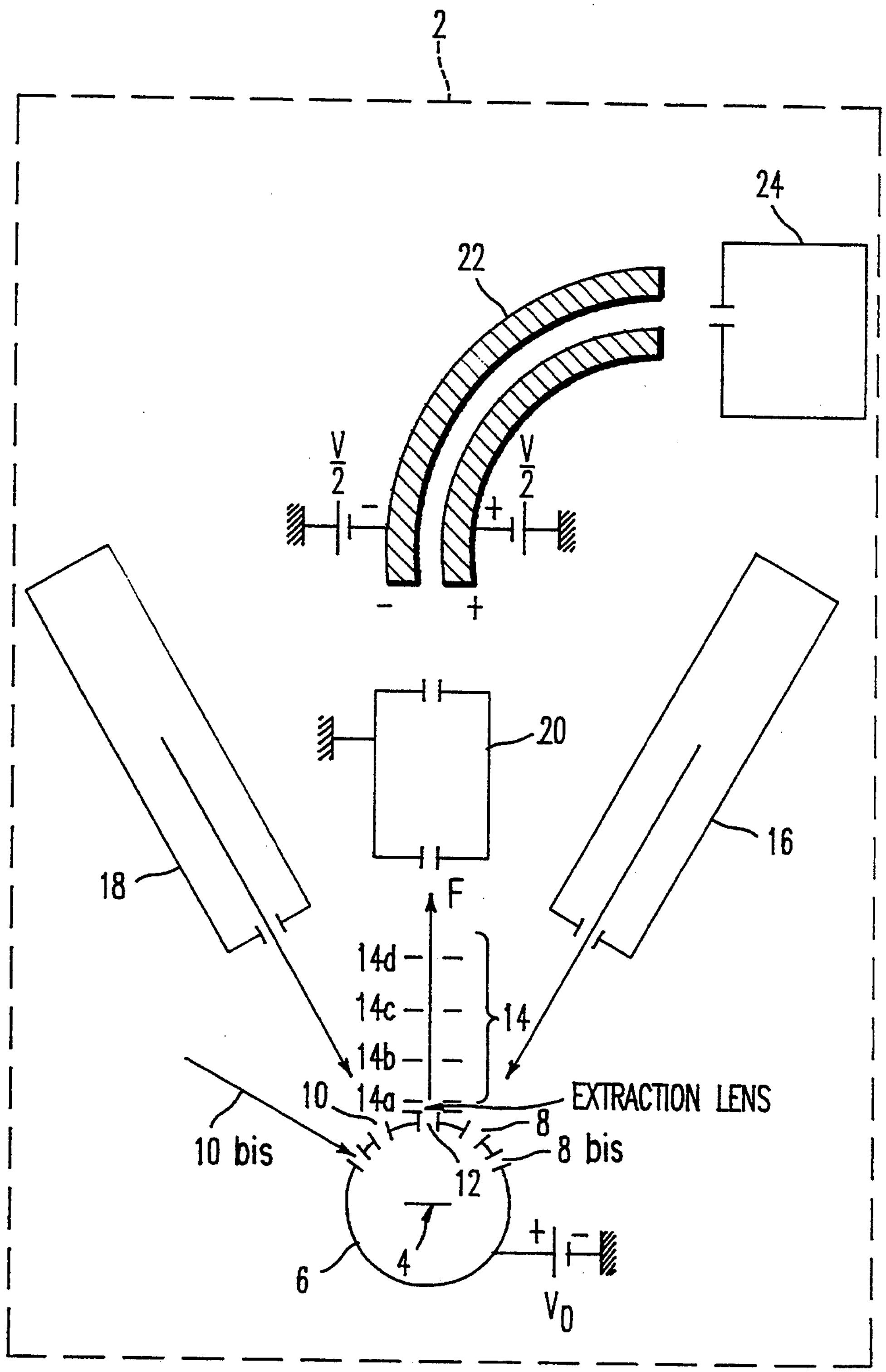
FIG. 1 Very diagrammatically an apparatus permitting the performance of the process according to the invention.

The following equipments are located in said enclosure. The target holder 4, which can be a small tank whose largest dimension does not exceed 20 mm and which can contain a liquid, a solid in powder form or in block (the target holder being different in the case of gases or aerosols). Hereinafter the term target is used for the body or material simultaneously subject to the action of the two jets or beams. The target holder is included in a conductive enclosure 6, in principle a vertical cylinder portion having holes, which is raised to a high voltage $V_o$. The enclosure has five orifices or holes. namely the orifices 8 and 10 for the introduction of the molecular jets, **8*b* is for a direct vision system of the target by means of a system of optical lenses, 10*b* is for the introduction of a laser beam and 12 for the extraction of the molecular ions formed on the target 4. This extraction is brought about by means of a system of lenses 14, 14*a*, 14*b*, 14*c*, 14*d* raised to different potentials, the last 14*d*** being at zero potential.

Two molecular jet sources 16, 18 are required for performing the process. The source 16 or first jet supplies to the target 4, through the orifice 8, atoms and molecules of compounds whose reaction is to be studied in vacuo.

The second molecular jet 18 introduced through the orifice in enclosure 6 onto the target 4 a jet of neutral molecules obtained by charge exchange of an inert gas, such as e.g. argon, krypton or xenon. As stated hereinbefore, the function of the second molecular jet 18 is to bring about the in situ ionization, as soon as formed on the target 4, of the molecules resulting from the chemical reaction of the compounds introduced by the first molecular jet 16 both with one another or with the target and then they are subject to a sputtering action. The target 4 can either be foreign to the studied chemical reaction or can participate therein, such as is e.g. the case when it is made from carbon, which can react with the atoms and molecules of the molecular jet 16. When ionized by the jet 18, the molecules formed on the target 4 by chemical reaction are extracted by sputtering and by means of electrostatic lenses 14 along the path indicated by the arrow F and they enter a dissociation box or chamber 20 filled with a neutral gas, where they partly shatter into different fragments of secondary ions. According to the theory already developed in FR-A-2 622 699 and FR-A-2 655 149, the dissociation process of primary ions from the target 4 by impact on neutral gas molecules contained in the dissociation box 20 is as follows. A primary ion of mass M and unit charge e leaves the enclosure 6 with the energy $eV_O$, $V_O$ being the high voltage to which the enclosure 6 is raised. When dissociated in the dissociation box 20 into different secondary ions of mass $m_1$, $m_2$, $m_k$, each of the thus formed secondary ions carries with it part of the total energy of the incident ion M equal to $eV_O \cdot m_1/M$ and $eV_{O} \cdot m_2/M$ and $eV_{O} \cdot m_k/M$, which will be designated hereinafter by $eV''$. On leaving the dissociation box 20, said secondary ions enter the electrostatic analyzer 22, whose filtration energy is $eV''$. By varying the value $V''$, it is consequently possible to regulate the electrostatic analyzer to a single energy value of the ions which can pass through it. By varying $V''$ in this way, the filtration level of the electrostatic analyzer 22 is scanned and successive selection takes place of the different secondary ions of masses $m_1, m_2 \ldots m_k$, the ion of mass $m_k$ traversing the electrostatic analyzer when $eV''=eV_O m_k/M$ or $V''/V_O=m_k/M$. At the end of the passage, the secondary ions passing out of the electrostatic analyzer 22 penetrate a detector 24, which optionally permits their identification. As the decomposition diagram of the chemical molecules formed in the enclosure 6 is known beforehand, the presence of an adequate number of said secondary dissociation fragments makes it possible to affirm that the primary molecule of mass M was present on the target 4 at the time when the molecular jet 8 entered into action. Thus, it is possible to follow in a quasi-instantaneous manner the formation of molecules of mass M on the target 4 of the enclosure 6.

A description will now be given of the study of the formation of two large organic molecules as components of ribonucleic and deoxyribonucleic acids and therefore any living matter. This material is formed by bombarding pure graphite with a mixture of molecular jets of nitrogen, hydrogen and oxygen.

Figure 2:
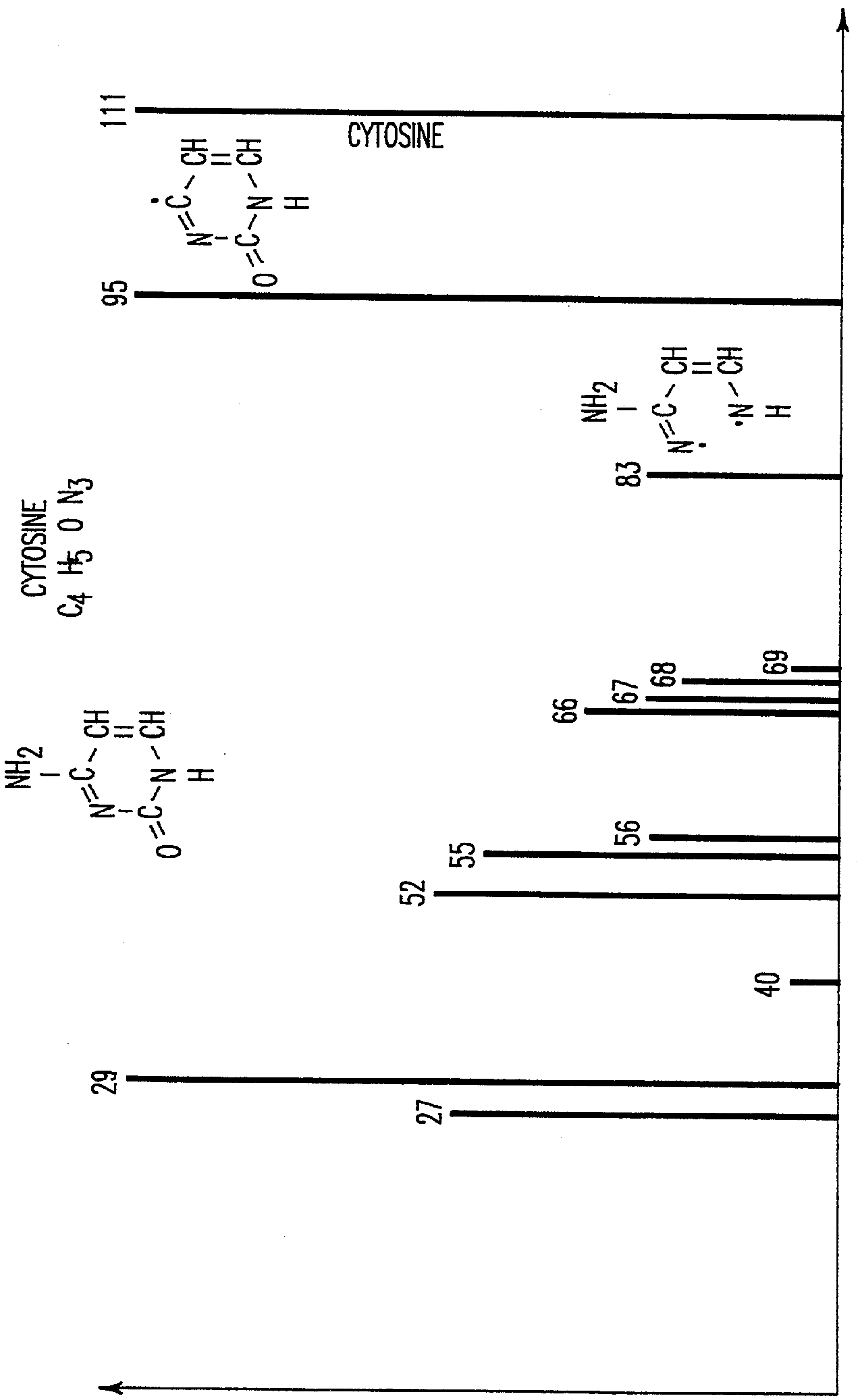
FIG. 2 The decomposition diagram with the secondary dissociation fragments of cytosine $C_4H_5ON_3$ obtained by synthesis in vacuo.

With reference to FIG. 2, a description will be given of the case of the cytosine molecule of general formula $C_4H_5ON_3$ and whose developed formula is:

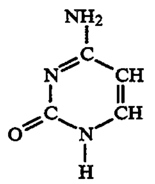

The diagram of FIG. 2 shows the peak of mass $M=111$ corresponding to cytosine and different dissociation fragments of said molecule and which are characteristic thereof.

Thus, it is possible to see the molecular peaks of mass 95 corresponding to the formula:

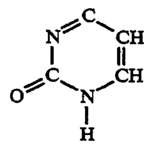

the molecular peak 83 corresponding to the formula:

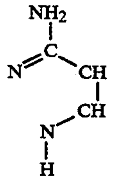

and different peaks of masses 69, 68, 67, 66, 56, 55, 52, 40, 29 and 27. The detection with the aid of the apparatus of FIG. 1 of a large number of these secondary peaks makes it possible to affirm that the cytosine molecule was present in the enclosure 6 at the time of the intervention of the molecular jet 18. It is pointed out that the indicated molecular masses sometimes differ by one or a few units from the mass corresponding to the chemical formula, due to the departure of a proton or even a group of atoms.

Figure 3:
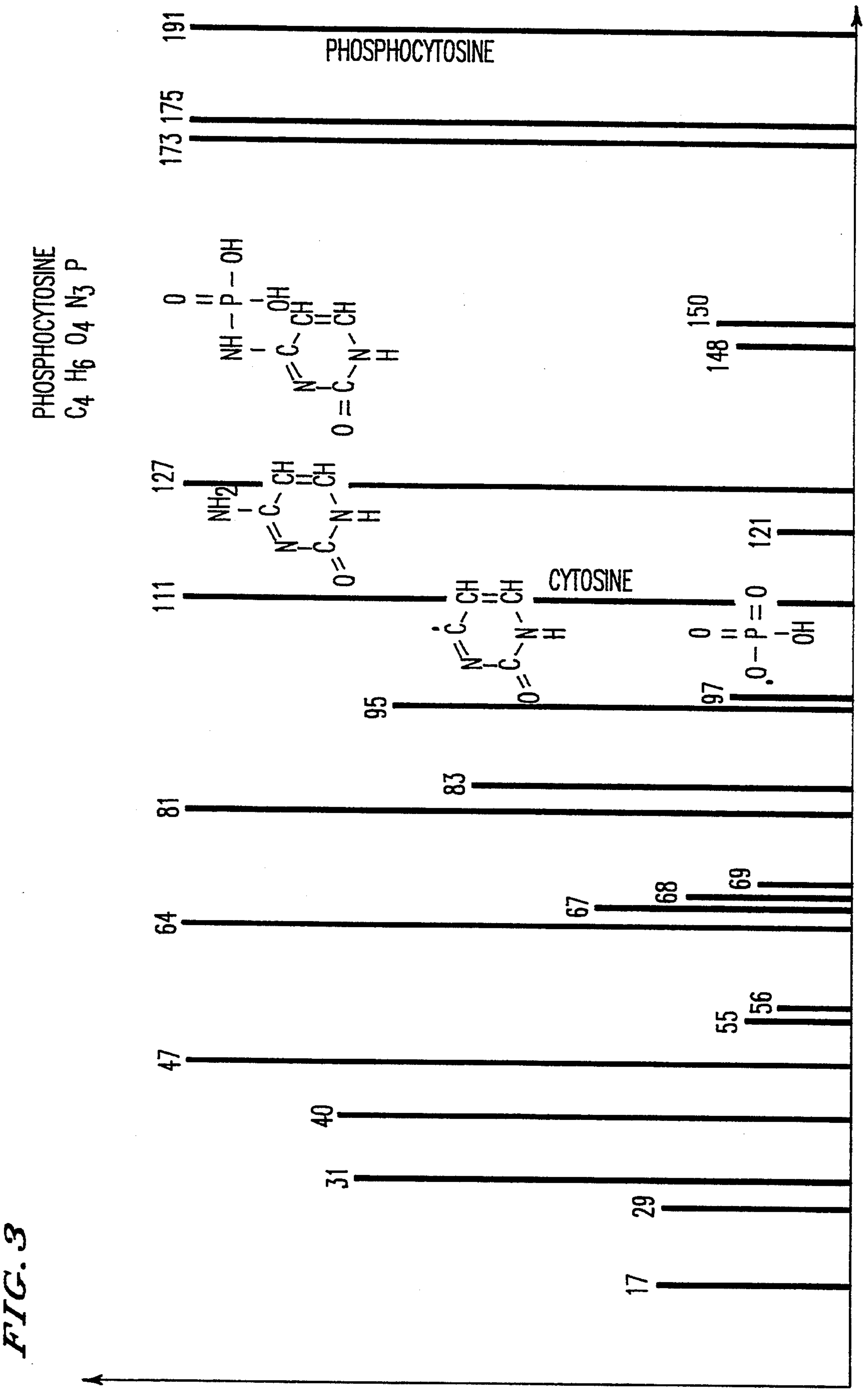
FIG. 3 The decomposition diagram in the form of dissociation fragments of phosphocytosine $C_4H_6O_4N_3P$.

FIG. 3 shows a decomposition diagram into secondary fragments of the same nature, but relative to phosphocytosine of general formula $C_4H_6O_4N_3P$ and of developed formula:

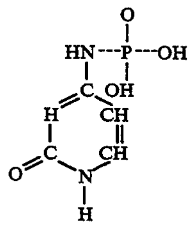

This material was obtained under the same conditions as hereinbefore, but with approximately 1 microgramme of pure phosphoric acid $PO_4H_3$, which was added to the graphite pellet prior to the experiment and using a special device.

The purity of the graphite is confirmed if, prior to the addition of phosphoric acid, using only the molecular gun 18, only carbon atoms and ions corresponding to the different clusters of the carbon up to e.g. $C^{14}$ lead the apparatus.

In accordance with what has been stated hereinbefore, the formation of phosphocytosine is studied by the apparatus of FIG. 1 by following the appearance of dissociation peaks of secondary mass 175, 173, 150, 148, 127 and 121, which have necessarily come from a dissociation of the phosphocytosine, because they are in the order of the masses of FIG. 3 upstream of the mass 111 of cytosine. If $V_O$ is used for designating the high voltage to which the enclosure 1 is raised, it is thus necessary to investigate by the filtration apparatus incorporating the analyzer 22 and the detector 24, the energies $eV_O.175/191$, $eV_O.173/191$, $eV_O.150/191$, etc. As soon as these energies are detected in the electrostatic analyzer, it is possible to affirm that a primary phosphocytosine molecule has formed in the enclosure 4 at the instant of the arrival of the molecular jet 10.

Another example of the performance of the process according to the invention e.g. relates to the study of the oxidation of a metal. With the aid of the apparatus of FIG. 1, a molecular jet of oxygen is supplied by the jet 16 to a metal target, whose oxidation is to be studied. It is possible to use a thermal molecular jet. It is thus possible to analyze the compounds formed, including clusters of metal, by dissociation. If X designates a divalent metal, whose primary ions in oxidized form can e.g. be XO, $X_2O$, $X_2O_2$, $X_3O_3$, etc., a study takes place of the formation of the secondary compounds, e.g. in $X_3$ and investigation occurs of the masses m, whose ratio m/M is equal to the values $X_3/X_3O$, $X_3O/X_3O_2$, etc.

In the particular case of tantalum which was studied in our laboratory about 10 years ago, e.g. using the cluster $Ta_4$:$Ta_4O_5$ and an oxygen pressure of $1.5\ 10^{-6}$ Torr, which dissociates as follows: $Ta_4O_4$, $Ta_4O_3$, $Ta_4O_2$, $Ta_4O$, this gives the ratios of the masses, i.e. filtered energies of 0.979, 0.959, 0.939 and 0.919. By means of the apparatus it is possible to follow the formation of these oxides by filtering the energy for a given ratio.

What is claimed is:

1. A process for the sequential observation of the successive states of a chemical reaction taking place in a vacuum by dissociation in a dissociation box (20) filled with neutral molecules of the compounds to be formed by chemical reaction, followed by energy filtration of the dissociation fragments in an electrostatic analyzer (22) and detector (24) comprising the steps of:

a) forming the molecules of the compounds to be analyzed on a target (4) in a conductive enclosure under vacuum held at a fixed DC potential; b) bombarding the target (4) by two molecular jet sources wherein the first molecular jet sources is a continuous jet source (16) which supplies the atoms and molecules which react with the target and a second pulsed inert gas jet source (18) to initiate in situ ionization of molecules formed on target (4) resulting from the chemical reaction of compounds introduced by the first continuous molecular jet source (16);

c) extracting the secondary ions formed on the target (4) by the secondary jet source by extraction lenses (14);

d) and passing said secondary ions to the intake of the dissociation box (2) wherein said secondary ions partly shatter into different fragments of secondary ions measurable by the electrostatic analyzer and detector permitting the sequential determination of a chemical reaction.

2. Analysis process according to claim 1, wherein the molecular jets have an energy of 0.5 to 15 keV and in that the vacuum enclosure (6) is raised to a voltage of 1000 to 15000 V.

3. Analysis process according to claim 1, wherein the second, intermittent molecular jet is a pulsed jet at a regulatable frequency.

4. Analysis process according to claim 1, wherein the vacuum enclosure (2, 6) is placed under a vacuum of approximately $10^{-9}$ to $10^{-6}$ Torr.

* * * * *